United States Patent [19]

Weferling

[11] Patent Number: 4,885,393

[45] Date of Patent: Dec. 5, 1989

[54] NOVEL S-BUTYL-DI-N-ALKYL PHOSPHINES, PHOSPHINE OXIDES AND PHOSPHINE SULFIDES, AND PROCESSES FOR MAKING THEM

[75] Inventor: Norbert Weferling, Hürth, Fed. Rep. of Germany

[73] Assignee: Hoechst Aktiengesellschaft, Frankfurt, Fed. Rep. of Germany

[21] Appl. No.: 339,163

[22] Filed: Apr. 17, 1989

Related U.S. Application Data

[63] Continuation of Ser. No. 77,222, Jul. 24, 1987, abandoned.

[30] Foreign Application Priority Data

Aug. 8, 1986 [DE] Fed. Rep. of Germany ....... 3626969

[51] Int. Cl.$^4$ .............................. C07F 9/50; C07F 9/53
[52] U.S. Cl. ............................................ 568/8; 568/14
[58] Field of Search ...................................... 568/8, 14

[56] References Cited

U.S. PATENT DOCUMENTS

| | | | |
|---|---|---|---|
| 2,138,835 | 12/1938 | Butz | 568/14 |
| 2,160,840 | 6/1939 | Dreyfus | 568/8 |
| 4,452,716 | 6/1984 | Cummins et al. | 568/14 |
| 4,575,563 | 3/1986 | Gunkel | 568/14 |

FOREIGN PATENT DOCUMENTS

| | | | |
|---|---|---|---|
| 0095453 | 11/1983 | European Pat. Off. | 568/14 |
| 899040 | 12/1953 | Fed. Rep. of Germany | 568/14 |

OTHER PUBLICATIONS

Rauhut, M. M. et al., J. Org. Chem., 26, pp. 5138–5145, (1961).

*Primary Examiner*—Paul F. Shaver

[57] ABSTRACT

Novel s-butyl-di-n-alkyl phosphines, phosphine oxides and phosphine sulfides of the general formula

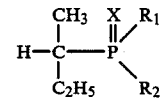

in which $R_1$ and $R_2$ each stand for identical or different, linear, unsubstituted alkyl chains having 5, 6, 8 or 10 carbon atoms, and X stands for a lone pair of electrons, oxygen or sulfur, and intermolecular mixtures of these compounds are disclosed, as well as processes for making them.

7 Claims, No Drawings

NOVEL S-BUTYL-DI-N-ALKYL PHOSPHINES, PHOSPHINE OXIDES AND PHOSPHINE SULFIDES, AND PROCESSES FOR MAKING THEM

This is a continuation of our copending application Ser. No. 07/077,222, filed July 24, 1987, now abandoned.

This invention relates to novel s-butyl-di-n-alkyl phosphines, s-butyl-di-n-alkyl phosphine oxides and s-butyl-di-n-alkyl phosphine sulfides, and to processes for making them.

Tertiary phosphines can be made by reacting hydrogen phosphide with an olefin.

Tertiary phosphine oxides are obtainable by subjecting the tertiary phosphines to an oxidation reaction.

German Specification DE-PS 899 040 describes a process, wherein equivalent quantities of hydrogen phosphide and an olefin are reacted at increased temperature in the presence of a peroxidic catalyst. The reaction product is a mixture consisting of about 85 wgt % trialkyl phosphine and about 15 wgt % monoalkyl phosphine or dialkyl phosphine.

In Journal of Organic Chemistry (1961), vol. 26, page 5139, it has been reported that the use of a stoichiometric excess of hydrogen phosphide permits the formation of trialkyl phosphines to be repressed in favor of the formation of monoalkyl phosphines.

As disclosed in European Specification 0 095 453 A2, s-butyl-di-(3-hydroxypropyl)-phosphine is obtained by a process, wherein hydrogen phosphide is reacted with butene-2 at 85°–90° C. in the presence of azo-di-isobutyronitrile as a radical-yielding agent, and the resulting intermediary product is reacted with allyl alcohol at 85°–90° C., again in the presence of azo-di-isobutyronitrile.

The phosphine so obtained is distilled under vacuum and oxidized with hydrogen peroxide in isopropanol. The product so obtained is purified and a mixture consisting of s-butyl-di-(3-hydroxypropyl)-phosphine oxide and 3-hydroxypropyl-di-s-butyl phosphine oxide is ultimately obtained, which is suitable for use as a flame-retardant agent for plastics materials.

As has been found, this prior phosphine oxide mixture is not fully satisfactory in respect of the following points:

It is more soluble in water than in unpolar solvents; it is not as regularly distributed in the plastics material as it would be desirable for a flame-retardant agent; if applied superficially, e.g. to a fabric, the readily water-soluble flame-retardant agent is liable to be washed out.

The present invention now provides novel compounds which are free from the adverse effects described hereinabove and which comprise s-butyl-di-n-alkyl phosphines, phosphine oxides and phosphine sulfides of the general formula

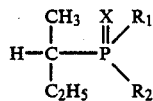

in which $R_1$ and $R_2$ each stand for identical or different, linear, unsubstituted alkyl chains having 5, 6, 8 or 10 carbon atoms, and X stands for a lone pair of electrons, oxygen or sulfur, and mixtures of those compounds.

The aforesaid compounds comprise more specifically: s-butyl-di-n-pentyl phosphine, s-butyl-di-n-pentyl phosphine oxide, and s-butyl-di-n-pentyl phosphine sulfide; s-butyl-di-n-hexyl phosphine, s-butyl-di-n-hexyl phosphine oxide, and s-butyl-di-n-hexyl phosphine sulfide; s-butyl-di-n-octyl phosphine, s-butyl-di-n-octyl phosphine oxide, and s-butyl-di-n-octyl phosphine sulfide; s-butyl-di-n-decyl phosphine, s-butyl-di-n-decyl phosphine oxide, and s-butyl-di-n-decyl phosphine sulfide.

They also comprise e.g. the following novel intermolecular mixtures:

s-butyl-n-hexyl-n-octyl phosphine with s-butyl-di-n-hexyl phosphine and s-butyl-di-n-octyl phosphine; s-butyl-n-hexyl-n-octyl phosphine oxide with s-butyl-di-n-hexyl phosphine oxide and s-butyl-di-n-octyl phosphine oxide; and s-butyl-n-hexyl-n-octyl phosphine sulfide with s-butyl-di-n-hexyl phosphine sulfide and s-butyl-di-n-octyl phosphine sulfide.

Intramolecularly different phosphines, their oxides and sulfides, as e.g. s-butyl-n-hexyl-n-octyl phosphine with three different R-radicals, its oxide and/or sulfide, are obtainable only in the intramolecular mixture aforesaid presenting approximately the following composition:

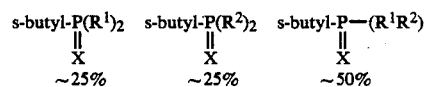

The present invention also relates to the following processes which permit all of the compounds aforesaid to be obtained with good purity and in high yields.

The process for making the s-butyl-di-n-alkyl phosphines of the general formula

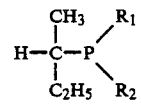

in which $R_1$ and $R_2$ each stand for identical or different, linear, unsubstituted alkyl chains having from 2 to 16 carbon atoms, especially 5, 6, 8 or 10 carbon atoms, comprises reacting s-butyl phosphine with a stoichiometric excess of an straight-chain 1-alkene at elevated temperature and under pressure, if desired, in the presence of a radical-yielding agent to give s-butyl-di-n-alkyl phosphine, and subjecting the reaction product to distillative work-up.

Preferred features of the process provide:

for the reaction to be effected using the straight-chain 1-alkene in an excess 2–10 times the molar quantity of s-butyl phosphine;

for the reaction to be effected at a temperature of 50°–120° C. and in the event of the straight-chain 1-alkene used being ethylene, propene, butene or pentene, under a pressure between 100 and 2 bars;

for azobisisobutyronitrile or azobisvaleronitrile to be used as the radical-yielding agent (free radical initiator); and for a mixture of straight-chain 1-alkenes with 5, 6, 8 or 10 carbon atoms, e.g. a mixture consisting of about 50 mol% n-octene-1 and 50 mol% 1-hexene, to be used as one of the reactants.

The process for making s-butyl-di-n-alkyl phosphine oxides of the general formula

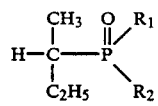

in which $R_1$ and $R_2$ each stand for identical or different, linear, unsubstituted alkyl chains having from 2 to 16 carbon atoms, especially 5, 6, 8 or 10 carbon atoms, comprises reacting a suitable s-butyl-di-n-alkyl phosphine with a slight stoichiometric excess of an about 30 wgt % hydrogen peroxide solution.

A preferred feature of that process provides for the reaction to be effected while cooling and with agitation and for the reaction product to be subjected to post-reaction at about 60°–90° C.

The process for making s-butyl-di-n-alkyl phosphine sulfides of the general formula

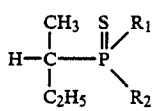

in which $R_1$ and $R_2$ each stand for identical or different, linear, unsubstituted alkyl chains having up to 16 carbon atoms, especially 5, 6, 8 or 10 carbon atoms, comprises reacting a suitable s-butyl-di-n-alkyl phosphine with elementary sulfur.

Preferred features of that process provide:
for the reaction to be effected at room temperature and for the reaction product to be subjected to post-reaction at about 80°–120° C.;
for suspended flowers of sulfur to be used and in this case, for the reaction to be effected using an equimolar quantity of sulfur, based on the s-butyl-di-n-alkyl phosphine.

The s-butyl-di-n-alkyl phosphines used as the feed materials for making the s-butyl-di-n-alkyl phosphine oxides and s-butyl-di-n-alkyl phosphine sulfides referred to hereinabove are made by the process of this invention as disclosed herein.

The novel products of this invention are useful flame-retardant agents.

The following Examples illustrate the invention which is naturally not limited thereto. cl EXAMPLE 1

Preparation of sec.-butyl phosphine

A 600 ml laboratory autoclave was charged initially with a solution of 1.65 g azobisisobutyronitrile (ABIN) in 60 ml toluene and then with 56 g (1 mol) 2-butene and 68 g (2 mol) $PH_3$ in the sequential order indicated. The reaction was initiated by heating the magnetically stirred mixture to 80° C. An initially slight exothermal behaviour and a gradual pressure decrease from 37 to 30 bars indicated that the reaction went on. After a reaction period of 8 hours at 80°–85° C., the autoclave was cooled with release of pressure, and purged with nitrogen. The crude product (120 g) was distilled at atmospheric pressure.

Bp: 72°–74° C.

Yield: 38 g (42%, based on the cis- or trans-butene used)

$31_{P-NMR}$: 113 ppm (>98 mol %)

EXAMPLE 2

Preparation of sec.-butyl-di-n-octyl phosphine 75 g (0.8 mol) sec.-butyl phosphine, 900 ml (5.2 mol) octene-1 and 1.8 g (11 millimol) ABIN were placed in a 2-liter flask with stirrer, reflux condenser and dropping funnel, and heated to 80° C. Next, a solution of 6.2 g ABIN in 400 ml octene was added dropwise within 3 hours. The temperature was maintained at 80°–85° C. over a period of 8 hours, and the reaction product was ultimately distilled under reduced pressure. Low boiling matter was removed and 190 g of a liquid colorless product was obtained.

Bp: 152°–156° C./0.5 millibar

Yield: 183 g (73%, based on phosphine used)

$31_{P-NMR}$: −19.2 ppm (>99 mol %)

EXAMPLE 3

Preparation of sec.-butyl-di-n-octyl phosphine oxide 40 g $H_2O_2$ (0.35 mol, 30% solution) was added dropwise while cooling with water and with intense agitation to 80 g (0.25 mol) sec.-butyl-di-n-octyl phosphine in a 500 ml-double-walled vessel. After all had been added, the reaction solution was heated to 70° C. over a period of 30 minutes, while stirring was interrupted. An aqueous phase which deposited on the bottom of the vessel was separated. It was admixed with 4.5 ml sodium carbonate solution (30 g/l) and the pH increased from 5.6 to 9.2. The whole was stirred over a period of 1 hour at 80° C. and allowed to deposit. The aqueous phase was separated and the crude product was distilled in vacuum.

Bp: 166°–168° C./0.5 millibar

Yield: 80.4 g (99.5% of the theoretical)

$31_{P-NMR}$: +47.3 ppm (>97 mol %)

EXAMPLE 4

Preparation of sec.-butyl-di-n-octyl phosphine sulfide 31.4 g (0.1 mol) sec.-butyl-di-n-octyl phosphine was admixed at room temperature with 3.2 g (0.1 mol) flowers of sulfur. An exothermal reaction immediately commenced taking place with consumption of the initially suspended sulfur; after the reaction had subsided, the whole was allowed to undergo post-reaction at 100° C. A clear yellow reaction mixture was obtained. $^{31}P$-NMR-spectroscopy evidenced the presence of merely one product. The crude product was distilled under vacuum.

Bp: 179°–183° C./0.3 millibar

Yield: 32.1 g (93% of the theoretical)

The product crystallized in the receiver.

$31_{P-NMR}$: +55.9 ppm

EXAMPLE 5

Preparation of a phosphine mixture

$R^1=R^2=$n-hexyl, about 25 mol %; $R^1=R^2=$n-octyl, about 25 mol %; $R^1=$n-hexyl, $R^2=$n-octyl, about 50 mol %.

92 g (1.03 mol) sec.-butyl phosphine, 116 g (1.4 mol) hexene-1 and 154 g (1.4 mol) octene-1 were mixed and heated to 70° C. in a 1-liter flask provided with a stirrer, reflux condenser, dropping funnel and internal diameter. Next, a mixture of 84 g hexene-1 and 112 g octene-1 containing 17 g dissolved azobisvaleronitrile (V65®, this is a registered Trade Mark of Wako Chemicals, JP) was added dropwise within 4 hours. The whole reaction period was 8 hours. All low boilers were removed under oil pump vacuum at a still temperature of 120° C., as soon as 31$_{P\text{-}NMR}$-spectroscopy indicated that the reaction was complete. The yield of crude product was 288 g (98% of the theoretical). The whole quantity was oxidized as in Example 3 using 114 g of a H$_2$O$_2$-solution of 30% strength and the resulting product (294 g=97% of theoretical) was distilled under vacuum.

BP: 125°–180° C./0.3 millibar

Yield: 281 g (90%, based on the sec.-butyl phosphine used)

$^{31}$P-NMR: 48.0 ppm

GC-analysis: 22.1% sec.-butyl-di-n-hexyl phosphine oxide, 49.2% sec.-butyl-n-hexyl-n-octyl phosphine oxide, 28.3% sec.-butyl-di-n-octyl phosphine oxide, 0.4% unidentified compounds

EXAMPLE 6

Preparation of sec.-butyl-di-n-pentyl phosphine 45 g (0.5 mol) sec.-butyl phosphine, 4.1 g (5 mol, based on the phosphine used) ABIN and 325 g (4.8 mol) pentene-1 were placed in a 600-milliter autoclave and heated to 80°–90° C. over a period of 6 hours. Pentene-1 in excess was distilled off at atmospheric pressure and the crude product was rectified under vacuum.

Bp: 105°–108° C./5 millibars

Yield: 99 g (86% of the theoretical) 31$_{P\text{-}NMR}$: −18.4 ppm (>98 mol %)

EXAMPLE 7

Preparation of sec.-butyl-di-n-pentyl phosphine oxide

As described in Example 3, 90 g (0.39 mol) sec.-butyl-di-n-pentyl phosphine was oxidized with 50 g (0.49 mol) of a 30% H$_2$O$_2$-solution. The product obtained was worked up distillatively.

Bp: 115°–121° C./0.4 millibar

Yield: 88 g (92% of the theoretical)

31$_{P\text{-}NMR}$: +47.6 ppm (>98 mol %).

We claim:

1. Sec-butyl-di-n-alkyl phosphine, phosphine oxide or phosphine sulfide of the formula

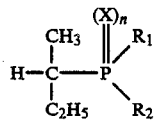

in which R$_1$ and R$_2$ each is each a linear, unsubstituted alkyl chain having 5, 6, 8 or 10 carbon atoms, X is oxygen or sulfur, and n is zero or 1.

2. A process for making sec-butyl-di-n-alkyl phosphine of formula

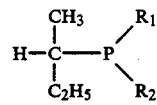

in which R$_1$ and R$_2$ is each a linear, unsubstituted alkyl chain having 2 to 16 carbon atoms, which comprises reacting sec-butyl phosphine with a stoichiometric excess, based on the sec-butyl phosphine, of a suitable 1-alkene, at a temperature of 50° to 120° C. and under greater-than-ambient pressure, in the presence of azobisisobutyronitrile or azobisvaleronitrile, and recovering sec-butyl-di-n-alkyl phosphine.

3. The process as claimed in claim 2, wherein the reaction is effected using a 1-alkene having 5, 6, 8 or 10 carbon atoms in a 2 to 10 times molar excess, based on the sec-butyl phosphine.

4. The process as claimed in claim 2, wherein a mixture of 1-alkenes, having 5, 6, 8 or 10 carbon atoms, is used.

5. The process as claimed in claim 2, wherein the reaction is conducted under a pressure between 100 and 2 bars.

6. A process for making sec-butyl-di-n-alkyl phosphine oxide of formula

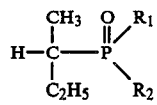

in which R$_1$ and R$_2$ each is each a linear, unsubstituted alkyl chain having 5, 6, 8 or 10 carbon atoms, which comprises reacting a suitable sec-butyl-di-n-alkyl phosphine of claim 2 with a slight stoichiometric excess, based on the introduced sec-butyl-di-n-alkyl phosphine, of 30 wgt.% hydrogen peroxide solution while cooling and with agitation and the reaction product is ultimately heated at a temperature between 60° and 90° C. over a period of 30 minutes.

7. A process for making sec-butyl-di-n-alkyl phosphine sulfides of formula

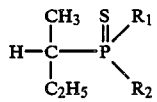

in which R$_1$ and R$_2$ is each a linear, unsubstituted alkyl chain having 5, 6, 8 or 10 carbon atoms, which comprises reacting a suitable sec-butyl-di-n-alkyl phosphine of claim 2 with sulfur, using approximately an equimolar quantity of sulfur, based on the sec-butyl-di-n-alkyl phosphine, at room temperature and the reaction product is ultimately heated to a temperature between 80° and 120° C. until the reaction is finished.

* * * * *